(12) United States Patent
Kampa et al.

(10) Patent No.: US 8,012,143 B1
(45) Date of Patent: Sep. 6, 2011

(54) INTRAPERICARDIAL DELIVERY TOOLS AND METHODS

(75) Inventors: Greg Kampa, Castaic, CA (US); Anna Barlow, Santa Clarita, CA (US); Kevin L. Morgan, Simi Valley, CA (US); Michael Yang, Thousand Oaks, CA (US); Steven R. Conger, Agua Dulce, CA (US); Stuart Rosenberg, Canyon Country, CA (US); Wenbo Hou, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 684 days.

(21) Appl. No.: 11/609,751

(22) Filed: Dec. 12, 2006

(51) Int. Cl.
*A61M 25/00* (2006.01)
(52) U.S. Cl. .............. 604/532; 604/96.01; 604/525; 604/264
(58) Field of Classification Search .......... 604/264, 604/96.01, 525, 532, 530; 607/122, 119, 607/129–132
See application file for complete search history.

(56) References Cited

U.S. PATENT DOCUMENTS

| | | | | |
|---|---|---|---|---|
| 3,896,804 A | * | 7/1975 | Ekbladh et al. ............ | 604/174 |
| 3,952,742 A | * | 4/1976 | Taylor ..................... | 604/21 |
| 4,865,037 A | | 9/1989 | Chin et al. | |
| 4,991,578 A | | 2/1991 | Cohen | |
| 4,998,975 A | | 3/1991 | Cohen et al. | |
| 5,188,605 A | * | 2/1993 | Sleep ...................... | 604/158 |
| 5,215,540 A | * | 6/1993 | Anderhub ................. | 604/532 |
| 5,312,355 A | * | 5/1994 | Lee ......................... | 604/160 |
| 5,336,252 A | | 8/1994 | Cohen | |
| 5,571,161 A | | 11/1996 | Starksen et al. | |
| 5,634,895 A | | 6/1997 | Igo et al. | |
| 5,653,730 A | * | 8/1997 | Hammerslag ............ | 606/214 |
| 5,716,392 A | | 2/1998 | Bourgeois et al. | |
| 5,840,059 A | | 11/1998 | March et al. | |
| 5,902,289 A | * | 5/1999 | Swartz et al. ............ | 604/530 |
| 5,997,525 A | | 12/1999 | March et al. | |
| 6,117,105 A | * | 9/2000 | Bresnaham et al. ...... | 604/96.01 |
| 6,132,417 A | * | 10/2000 | Kiesz ...................... | 604/523 |
| 6,224,584 B1 | | 5/2001 | March et al. | |
| 6,423,051 B1 | | 7/2002 | Kaplan et al. | |
| 6,524,298 B1 | | 2/2003 | March et al. | |
| 6,638,268 B2 | * | 10/2003 | Niazi ...................... | 604/528 |
| 6,659,950 B2 | | 12/2003 | Taheri | |
| 6,718,212 B2 | | 4/2004 | Parry et al. | |
| 7,288,096 B2 | | 10/2007 | Chin | |
| 7,398,781 B1 | | 7/2008 | Chin | |
| 7,526,342 B2 | | 4/2009 | Chin et al. | |

(Continued)

FOREIGN PATENT DOCUMENTS

WO 9725099 12/1996

(Continued)

OTHER PUBLICATIONS

NonFinal Office Action, mailed Jul. 6, 2009: Related U.S. Appl. No. 11/609,759.

(Continued)

*Primary Examiner* — Theodore Stigell

(57) ABSTRACT

An introducer sheath is disclosed herein. The sheath includes a tubular body. The tubular body has a proximal zone, an intermediate zone and a distal zone. The proximal zone is generally straight. The intermediate zone extends from a distal end of the proximal zone and curves in a first direction. The distal zone extends from a distal end of the intermediate zone and curves in a second direction different from the first direction.

24 Claims, 16 Drawing Sheets

U.S. PATENT DOCUMENTS

| | | |
|---|---|---|
| 7,621,904 B2 * | 11/2009 | McFerran et al. ............ 604/525 |
| 2002/0072737 A1 | 6/2002 | Belden et al. |
| 2002/0151868 A1 | 10/2002 | Taheri |
| 2003/0074041 A1 | 4/2003 | Parry et al. |
| 2003/0208141 A1 * | 11/2003 | Worley et al. ................. 600/585 |
| 2003/0212446 A1 | 11/2003 | Kaplan et al. |
| 2004/0102804 A1 | 5/2004 | Chin |
| 2004/0216748 A1 | 11/2004 | Chin |
| 2005/0102003 A1 | 5/2005 | Grabek et al. |
| 2005/0154376 A1 | 7/2005 | Riviere et al. |
| 2006/0106442 A1 | 5/2006 | Richardson et al. |
| 2006/0116746 A1 | 6/2006 | Chin |

FOREIGN PATENT DOCUMENTS

| | | |
|---|---|---|
| WO | 2004002288 A2 | 1/2004 |
| WO | 2004002288 A3 | 1/2004 |
| WO | 2005046461 A1 | 5/2005 |

OTHER PUBLICATIONS

NonFinal Office Action, mailed Feb. 4, 2010—Related U.S. Appl. No. 11/609,759.

Final Office Action, mailed Jul. 6, 2010—Related U.S. Appl. No. 11/609,759.

* cited by examiner

INTRAPERICARDIAL DELIVERY TOOLS AND METHODS

CROSS-REFERENCE TO RELATED APPLICATIONS

This application is related to copending U.S. patent application Ser. No. 11/609,759, file Dec. 12, 2006, titled "Intrapericardial Delivery Tools and Methods".

FIELD OF THE INVENTION

The present invention relates to medical apparatus and methods. More specifically, the present invention relates to tools and methods for intrapericardial subxiphoid access delivery of medical devices and therapy.

BACKGROUND OF THE INVENTION

Factors (e.g., coronary sinus obstructions, absence of a suitable cardiac vein, high thresholds, or phrenic nerve stimulation) warrant the need for an alternative to a transvenous approach to the implantation of some or all left ventricle ("LV"), left atrial ("LA"), right atrial ("RA") and right ventricle ("RV") leads in congestive heart failure ("CHF") patients in need of cardiac rhythm treatment ("CRT"). Historically, the alternative to a transvenous approach has entailed placement of an epicardial lead, which required invasive surgery and an associated hospital stay.

A minimally invasive pericardial approach to implanting a stimulating lead (e.g., a LV lead) has shown great promise as an alternative to the aforementioned transvenous and invasive surgery methods. In the pericardial approach, an introducer sheath is used to deliver a lead via a subxiphoid access to an implant location within the pericardial space. Visualization techniques, such as traditional fluoroscopy, MRI or endoscopy, are used to guide the introducer sheath to the implantation location within the pericardial space and to guide the final positioning of the lead.

For several reasons, the minimally invasive pericardial approach offers greater simplicity and safety as compared to the transvenous and surgical approaches to stimulation lead implantation. First, the pericardial approach does not require access to the vascular system. Second, it is minimally invasive and does not require surgical intervention and the associated general anesthesia. Third, it allows for a pathway to the entire exterior of the heart (e.g., any chamber, blood vessel or other anatomical feature of the heart) via a single entry point in the patient and in the pericardial sac.

While the pericardial approach allows for a pathway to the entire exterior of the heart, actually accessing the entire exterior of the heart via a delivery tool is another matter. Consequently, there is a need in the art for an introducer sheath that readily facilitates accessing the entire, or nearly the entire, exterior of the heart via a subxiphoid access. There is also a need in the art for a method of delivering a medical device or therapy to any point on the exterior of the heart.

BRIEF SUMMARY OF THE INVENTION

An introducer sheath is disclosed herein. In one embodiment, the sheath includes a tubular body. The tubular body has a proximal zone, an intermediate zone and a distal zone. The proximal zone is generally straight. The intermediate zone extends from a distal end of the proximal zone and curves in a first direction. The distal zone extends from a distal end of the intermediate zone and curves in a second direction different from the first direction.

An introducer sheath is disclosed herein. In one embodiment, the sheath includes a tubular body. The tubular body has a generally straight proximal zone and a curved distal zone. The proximal zone is more rigid than the distal zone.

An introducer is disclosed herein. In one embodiment, the introducer includes inner and outer sheaths coaxial with each other. A distal end of a curved tubular body of the inner sheath extends past a distal end of a curved tubular body of the outer sheath.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION

The present application describes an introducer sheath 10 for delivering a medical device and/or therapy to a pericardial space via a subxiphoid access, wherein the introducer sheath 10 is configured such that it can perform a full 360-degree sweep around the heart. More specifically, a distal zone 45 of the sheath 10 is configured to generally match or conform to the heart epicardial surface as the distal zone 45 performs a full 360-degree sweep (i.e., circumnavigates) about the heart epicardial surface circumference.

The sheath 10 is advantageous in that it facilitates a simple method of accessing the entire or nearly the entire exterior surface of the heart from a subxiphoid access. In other words, the distal zone 45 of the sheath 10 can be swept or made to displace along the exterior surfaces of generally any region of the heart, including the right and left ventricles and right and left atriums, while a proximal zone 35 of the sheath 10 extends through the subxiphoid access.

In sweeping or displacing about the heart, the distal zone 45 of the sheath 10 can move from any side of the heart to any other side of the heart (e.g., from the anterior to the posterior, or vice versa). While the sheath 10 is configured such that the distal zone 45 can sweep a full 360 degrees or more about the surface of the heart, the sheath 10 can be manipulated such that the sweep is less than 360 degrees. For example, a physician could limit the sweep to cover only five, ten or etc. degrees of the heart surface circumference. Ultimately, the sheath distal zone 45 can access any or nearly any region or side of the heart and displace (i.e., sweep) along the heart surface to another region or side of the heart while the proximal sheath zone 35 extends through the subxiphoid access.

Figure 1:
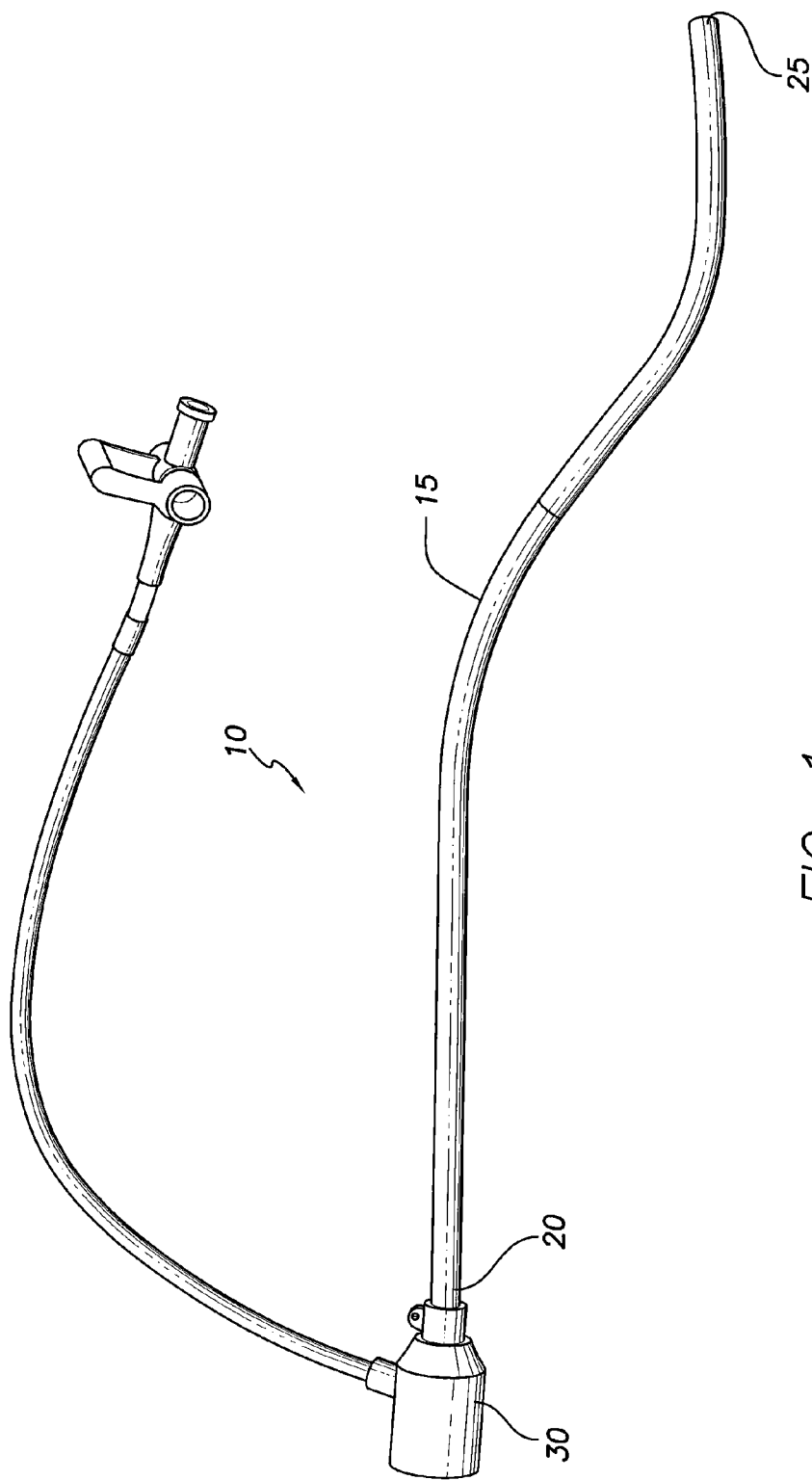
FIG. 1 is an overall view of a first embodiment of the introducer sheath and some of its various components.

For a discussion of a first embodiment of the introducer sheath 10, reference is made to FIG. 1, which is an overall view of the introducer sheath 10 and some of its various components. As shown in FIG. 1, in one embodiment, the introducer sheath 10 includes a tubular body 15, a proximal end 20, a distal end 25, and a hemostasis valve 30 coupled to the proximal end 20.

Figure 2:
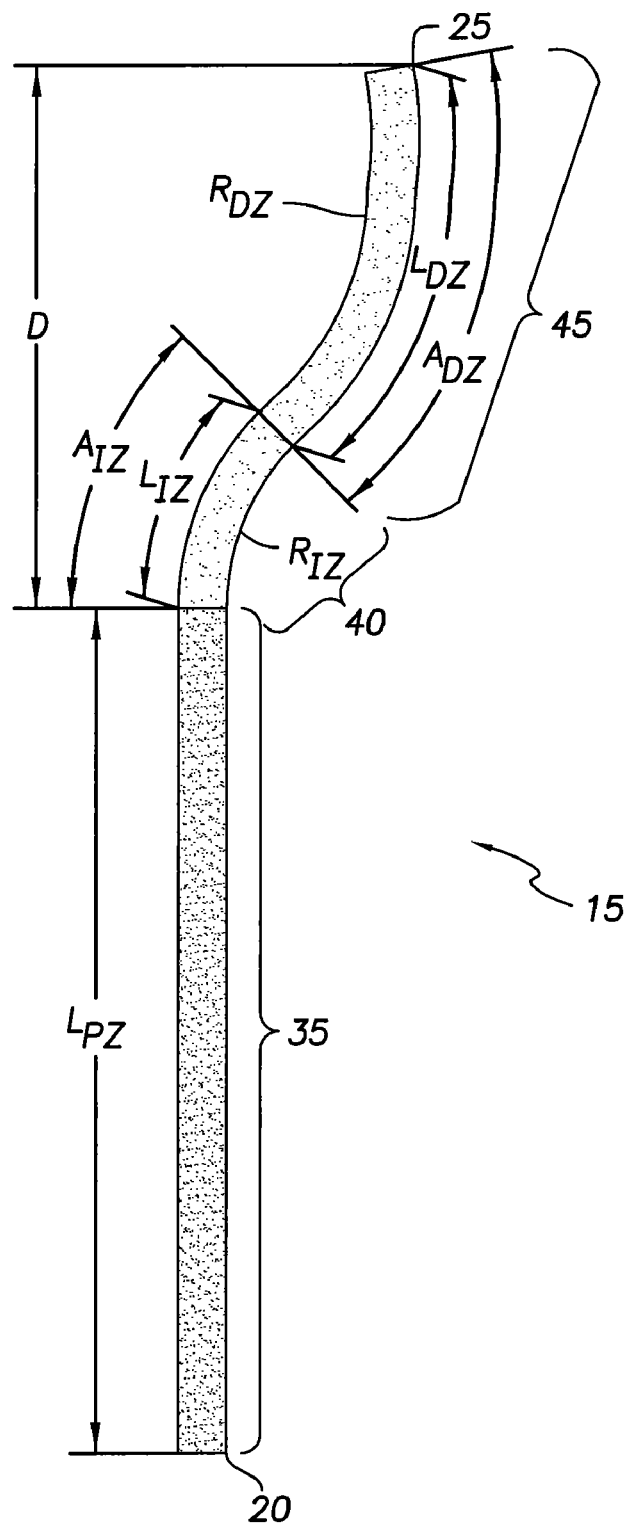
FIG. 2 is a plan view of the tubular body of the sheath depicted in FIG. 1.

As illustrated in FIG. 2, which is a plan view of the tubular body 15 of the sheath 10 depicted in FIG. 1, in one embodiment, the tubular body 15 includes a proximal zone 35, an intermediate or transition zone 40, and a distal zone 45. In one embodiment, the tubular body 15 has a diameter of between approximately 7 French and approximately 16 French. In one embodiment, the tubular body 15 will have a diameter that is less than 7 French. In one embodiment, the tubular body 15 will have a diameter of greater than 16 French. In one embodiment, the tubular body will have a diameter of 9 French. In one embodiment, the tubular body 15 will have a wall thickness of between approximately 0.005 inch and approximately 0.025 inch.

As indicated in FIG. 2, in one embodiment, the proximal zone 35 is generally straight and its distal end transitions into the intermediate zone 40, which curves in a first direction. The distal end of the intermediate zone 40 transitions into the distal zone 45, which curves in a second direction reversed to the curve direction of the intermediate zone 40. The combined effect of the curves of the intermediate and distal zones 40, 45 is that the tubular body distal end 25 points in a direction generally parallel to the longitudinal axis of the proximal zone 35. More specifically, in one embodiment, the tubular body distal end 25 ends up pointing in a direction that is anywhere from approximately zero degrees to approximately twenty degrees from being parallel to the longitudinal axis of the proximal zone 35. In one embodiment, the tubular body distal end 25 ends up pointing in a direction that is approximately ten degrees from being parallel to the longitudinal axis of the proximal zone 35.

As shown in FIG. 2, in one embodiment, the proximal zone 35 is generally straight and has a length $L_{PZ}$ of approximately 10 centimeters. In one embodiment, the length $L_{PZ}$ of the proximal zone 35 is between approximately eight centimeters and approximately 18 centimeters.

In one embodiment, the proximal zone 35 is formed of a polymer material such as polyether block amides ("PEBAX"), nylon, polyethylene, or etc. In one embodiment, the proximal zone 35 is formed of a polymer material having a durometer of between approximately 40 Shore D approximately 72 Shore D.

As indicated in FIG. 2, in one embodiment, the intermediate zone 40 is curved in a first direction and has a length $L_{IZ}$ of approximately 2.5 centimeters. In one embodiment, the length $L_{IZ}$ of the intermediate zone 40 is between approximately two centimeters and approximately six centimeters.

In one embodiment, the intermediate zone 40 curves over an angle $A_{IZ}$ of approximately 45 degrees. In one embodiment, the intermediate zone 40 curves over an angle $A_{IZ}$ of between approximately 30 degrees and approximately 60 degrees.

In one embodiment, the intermediate zone 40 curves over a radius $R_{IZ}$ of approximately 2.8 centimeters. In one embodiment, the intermediate zone 40 curves over a radius $R_{IZ}$ of between approximately two centimeters and approximately five centimeters.

In one embodiment, the intermediate zone 40 is formed of a polymer material such as PEBAX, nylon, polyethylene, or etc. In one embodiment, the intermediate zone 40 is formed of a polymer material that is less rigid than the polymer material of the proximal zone 35. In one embodiment, the intermediate zone 40 is formed of a material having a durometer of between approximately 35 Shore D approximately 72 Shore D.

As indicated in FIG. 2, in one embodiment, the distal zone 45 is curved in a second direction that is generally reversed from the direction of the curve of the intermediate zone 40. In one embodiment, the distal zone 45 has a length $L_{DZ}$ of approximately 4.8 centimeters. In one embodiment, the length $L_{DZ}$ of the distal zone 45 is between approximately two centimeters and approximately ten centimeters.

In one embodiment, the distal zone 45 curves over an angle $A_{DZ}$ of approximately 55 degrees. In one embodiment, the distal zone 45 curves over an angle $A_{DZ}$ of between approximately 30 degrees and approximately 85 degrees.

In one embodiment, the distal zone 45 curves over a radius $R_{DZ}$ of approximately 4.6 centimeters. In one embodiment, the distal zone 45 curves over a radius $R_{DZ}$ of between approximately two centimeters and approximately eight centimeters.

In one embodiment, the distal zone 45 is formed of a polymer material such as PEBAX, nylon, polyethylene, or etc. In one embodiment, the distal zone 45 is formed of a polymer material that is less rigid than the polymer material of the intermediate zone 40. In one embodiment, the distal zone 45 is formed of a material having a durometer of between approximately 25 Shore D approximately 72 Shore D.

As indicated in FIG. 2, in one embodiment, the distal end 25 of the tubular body 15 is offset from the distal end of the proximal zone 35 a linear distance D of approximately 6.4 centimeters. In one embodiment, the distal end 25 of the tubular body 15 is offset from the distal end of the proximal zone 35 a linear distance D of between approximately five centimeters and approximately 14 centimeters.

Figure 3A:
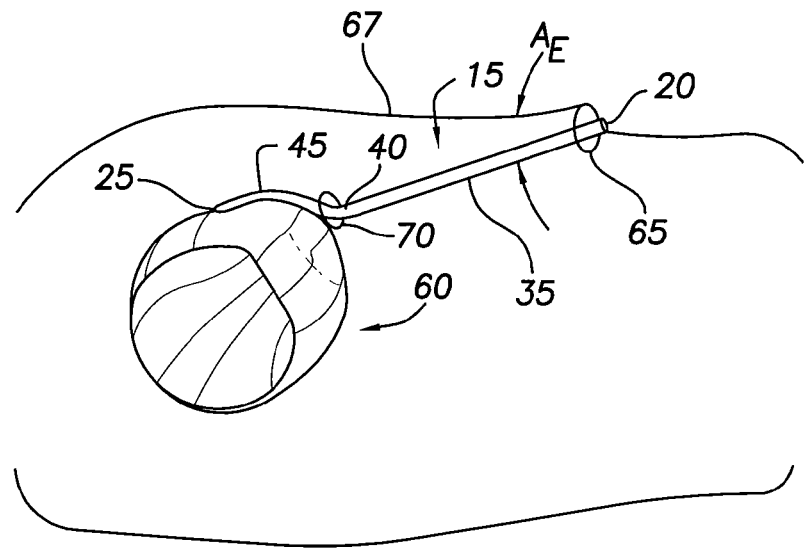
FIGS. 3A-3C illustrate various views of the first embodiment of the tubular body laying next to the left and right ventricle portions of a patient's heart as the tubular body makes an anterior approach to the heart from a subxiphoid opening in the patient's chest wall.
Figure 3B:
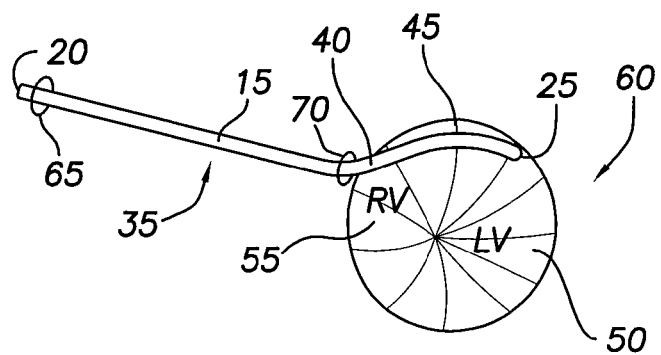
Figure 3C:
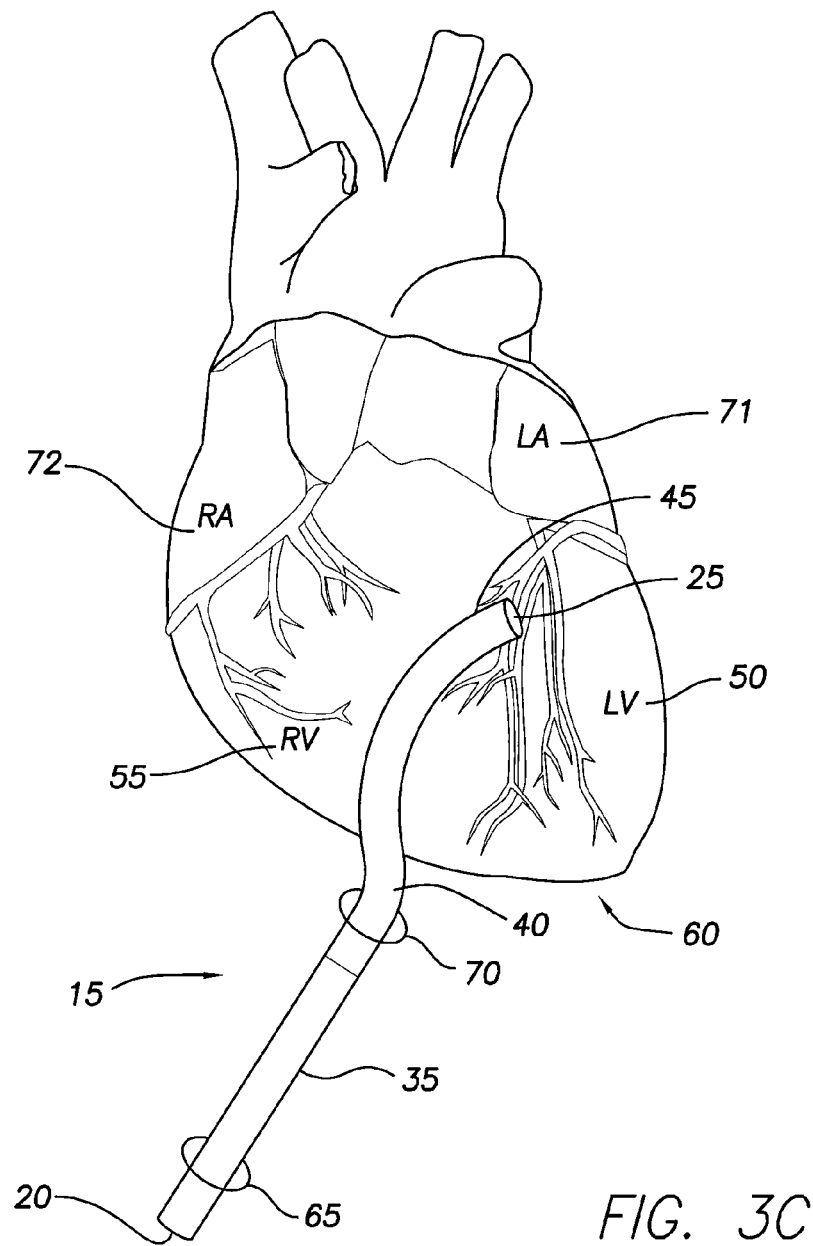
Figure 4A:
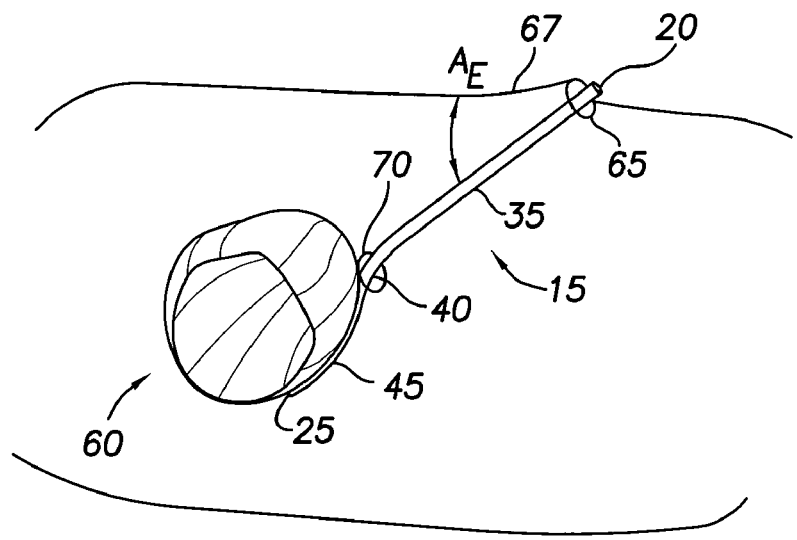
FIGS. 4A-4C illustrate various views of the first embodiment of the tubular body laying next to the left and right ventricle portions of a patient's heart as the tubular body makes a posterior approach to the heart from a subxiphoid opening in the patient's chest wall.
Figure 4B:
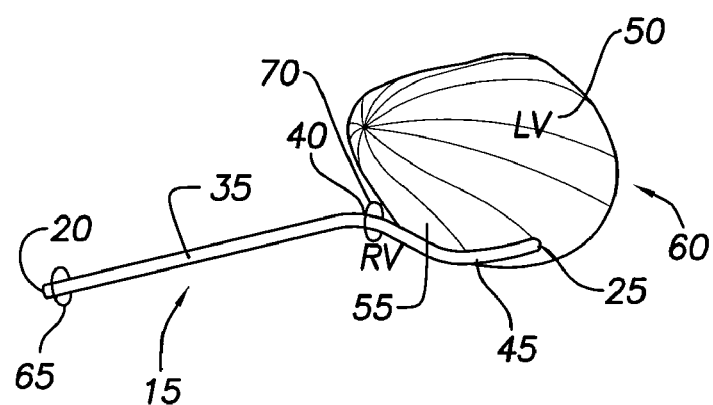
Figure 4C:
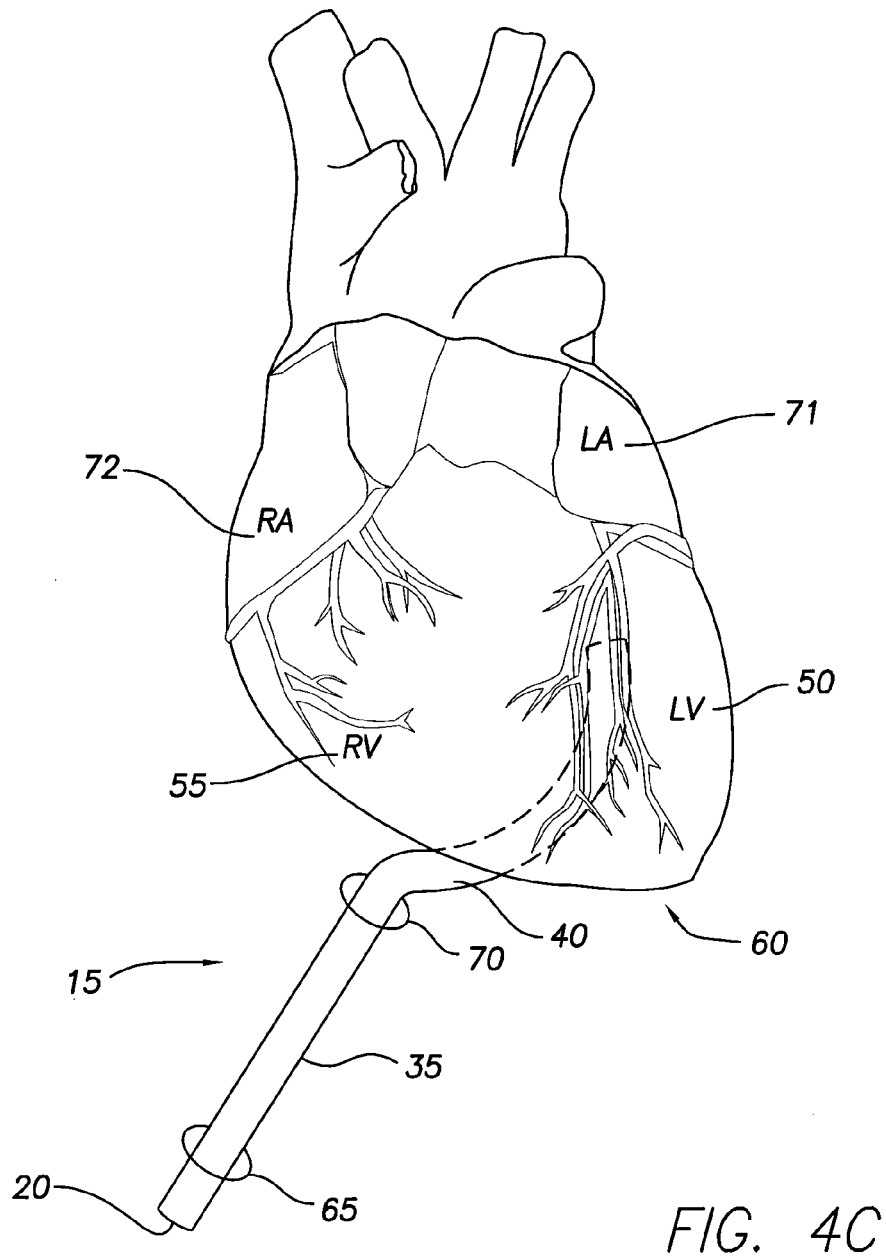

For an illustration of some of the advantages presented by the configuration of the tubular body 15 of the introducer sheath 10 depicted in FIGS. 1 and 2, reference is made to FIGS. 3A-3C and 4A-4C. FIGS. 3A-3C illustrate various views of the first embodiment of the tubular body 15 laying next to the left and right ventricle portions 50, 55 of a patient's heart 60 as the tubular body 15 makes an anterior approach to the heart 60 from a subxiphoid opening 65 in the patient's chest wall 67. FIGS. 4A-4C illustrate various views of the first embodiment of the tubular body 15 laying next to the left and right ventricle portions 50, 55 of a patient's heart 60 as the tubular body 15 makes a posterior approach to the heart 60 from a subxiphoid opening 65 in the patient's chest wall 67.

As can be understood in FIGS. 3A-3C and 4A-4C, in one embodiment, the tubular body 15 enters the subxiphoid opening 65 at a subxiphoid entry angle $A_E$ of between approximately 35 degrees and approximately 45 degrees. The curved portions 40, 45 of the tubular body 15 lie next to, and generally match, the heart ventricle surfaces 50, 55. The proximal zone 35 resides in the subxiphoid subcutaneous area, the intermediate zone 40 sits at the pericardial sac opening 70, and the distal zone 45 resides in the pericardial space.

Because of the curved configuration of the tubular body 15 and the differences in rigidity between the various zones 35, 40, 45 of the tubular body 15, the first embodiment of the tubular body 15 is able to sweep 360 degrees around the heart 60 within the pericardial sac. Also, the curved portions 40, 45 can be swept about the heart anterior to posterior, or vice versa. As a result, the first embodiment of the tubular body 15 can be used to deliver a medical device or therapy (e.g., pacing or defibrillation leads, myocardial infarction patches, ablation catheters, mapping catheters, fiber optic video cameras, drugs, etc.) to any location, or nearly any location, on the epicardial surface of the heart, including the right and left ventricle surfaces and the right and left atrium surfaces. Also, the first embodiment of the tubular body 15 can be used to gently loosen pericardial adhesions at any location, or nearly any location, in the pericardial space and prepare the pericardial space for delivery of the medical device and/or therapy. In one embodiment, the curved portions 40, 45 of the tubular body 15 are configured to lie next to, and generally match, the heart ventricle surfaces 50, 55 and/or the heart atrium surfaces 71, 72. In one embodiment, where the curved portions 40, 45 are configured to lie next to, and generally match, both the ventricle and atrium surfaces 50, 55, 71, 72, the curved portions 40, 45 are sufficiently supple to conforming adapt between the ventricle surfaces 50, 55 and the atrium surfaces 71, 72.

The double curve design depicted in FIGS. 1 and 2 can be used to allow some flexibility in medical device placement and maneuverability provided by the sheath 10. If the double curve tubular body 15 is slightly rotated clockwise or counterclockwise, the tubular body distal end 25 and medical device trajectories shift from side to side.

Figure 5:
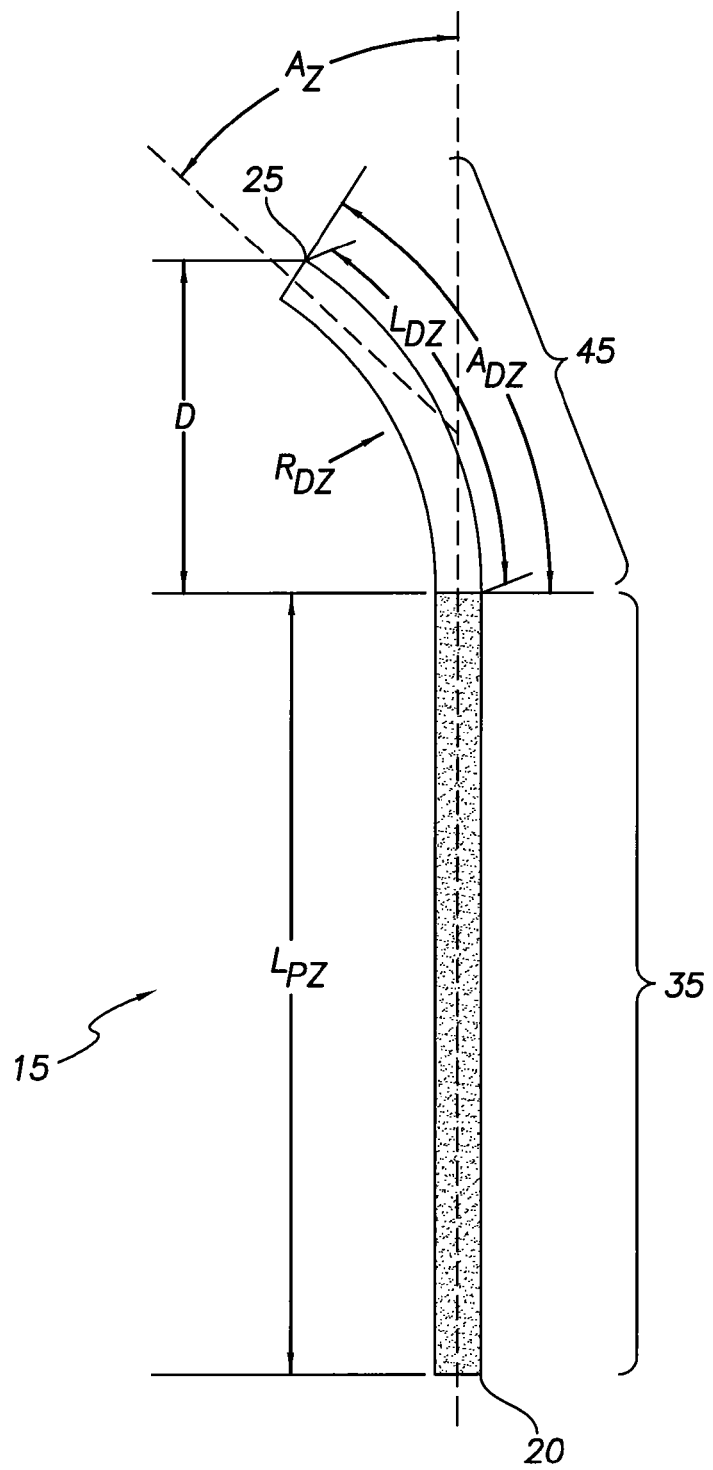
FIG. 5 is a plan view of a tubular body of a sheath similar to that depicted in FIG. 1, except the tubular body has a single curved zone.

For a discussion of a second embodiment of the introducer sheath 10, reference is made to FIG. 5, which is a plan view of a tubular body 15 of a sheath 10 similar to that depicted in FIG. 1, except the tubular body has a single curved zone. As shown in FIG. 5, in one embodiment, the tubular body 15 includes a proximal zone 35 and a distal zone 45. In one embodiment, the tubular body 15 has a diameter of between approximately 7 French and approximately 16 French. In one embodiment, the tubular body 15 will have a diameter that is less than 7 French. In one embodiment, the tubular body 15 will have a diameter of greater than 16 French. In one embodiment, the tubular body will have a diameter of 9 French. In one embodiment, the tubular body 15 will have a wall thickness of between approximately 0.005 inch and approximately 0.025 inch.

As indicated in FIG. 5, in one embodiment, the proximal zone 35 is generally straight and its distal end transitions into the distal zone 45, which curves in a first direction. Because of the curve of the distal zone 45, the tubular body distal end 25 points in a direction that is anywhere from approximately 20 degrees to approximately 60 degrees from being parallel to the longitudinal axis of the proximal zone 35, as indicated by angle $A_Z$ in FIG. 5. In one embodiment, the tubular body distal end 25 ends up pointing in a direction that is approximately 45 degrees from being parallel to the longitudinal axis of the proximal zone 35, as indicated by angle $A_Z$ in FIG. 5.

As shown in FIG. 5, in one embodiment, the proximal zone 35 is generally straight and has a length $L_{PZ}$ of approximately 15 centimeters. In one embodiment, the length $L_{PZ}$ of the proximal zone 35 is between approximately eight centimeters and approximately 18 centimeters.

In one embodiment, the proximal zone 35 is formed of a polymer material such as PEBAX, nylon, polyethylene, or etc. In one embodiment, the proximal zone 35 is formed of a polymer material having a durometer of between approximately 40 Shore D approximately 72 Shore D.

As indicated in FIG. 5, in one embodiment, the distal zone 45 is curved in a first direction and has a length $L_{DZ}$ of approximately eight centimeters. In one embodiment, the length $L_{DZ}$ of the distal zone 45 is between approximately seven centimeters and approximately 14 centimeters.

In one embodiment, the distal zone 45 curves over an angle $A_{DZ}$ of approximately 53 degrees. In one embodiment, the distal zone 45 curves over an angle $A_{DZ}$ of between approximately 30 degrees and approximately 60 degrees.

In one embodiment, the distal zone 45 curves over a radius $R_{DZ}$ of approximately seven centimeters. In one embodiment, the distal zone 45 curves over a radius $R_{DZ}$ of between approximately five centimeters and approximately 12 centimeters.

In one embodiment, the distal zone 45 is formed of a polymer material such as PEBAX, nylon, polyethylene, or etc. In one embodiment, the distal zone 45 is formed of a polymer material that is less rigid than the polymer material of the proximal zone 35. In one embodiment, the distal zone 45 is formed of a material having a durometer of between approximately 25 Shore D approximately 72 Shore D.

As indicated in FIG. 5, in one embodiment, the distal end 25 of the tubular body 15 is offset from the distal end of the proximal zone 35 a linear distance D of approximately three centimeters. In one embodiment, the distal end 25 of the tubular body 15 is offset from the distal end of the proximal zone 35 a linear distance D of between approximately two centimeters and approximately five centimeters.

For an illustration of some of the advantages presented by the configuration of the tubular body 15 of the introducer sheath 10 depicted in FIG. 5, reference is made to FIGS.

Figure 6A:
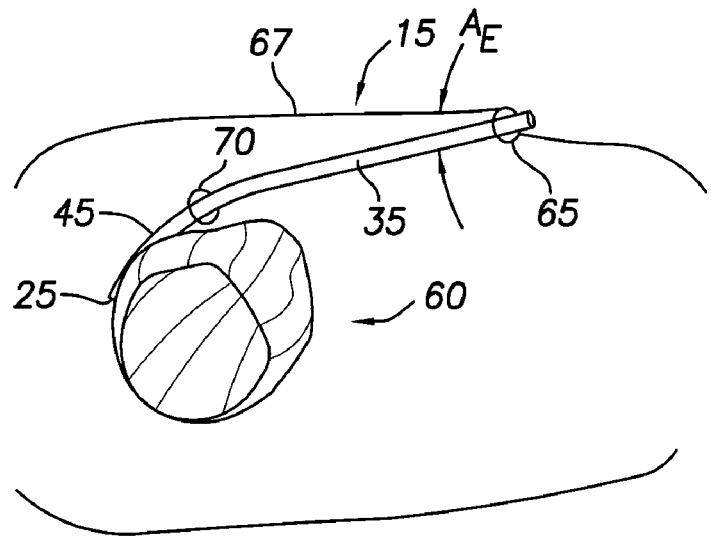
FIGS. 6A-6C illustrate various views of the second embodiment of the tubular body laying next to the left and right ventricle portions of a patient's heart as the tubular body makes an anterior approach to the heart from a subxiphoid opening in the patient's chest wall.
Figure 6B:
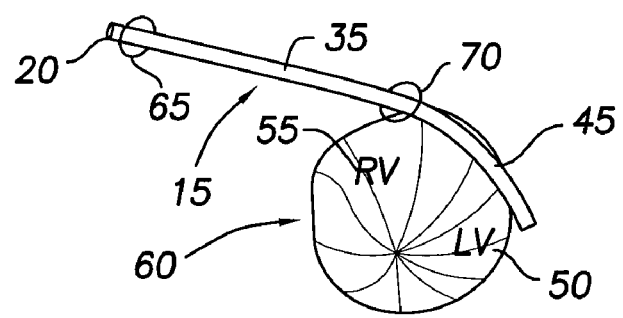
Figure 6C:
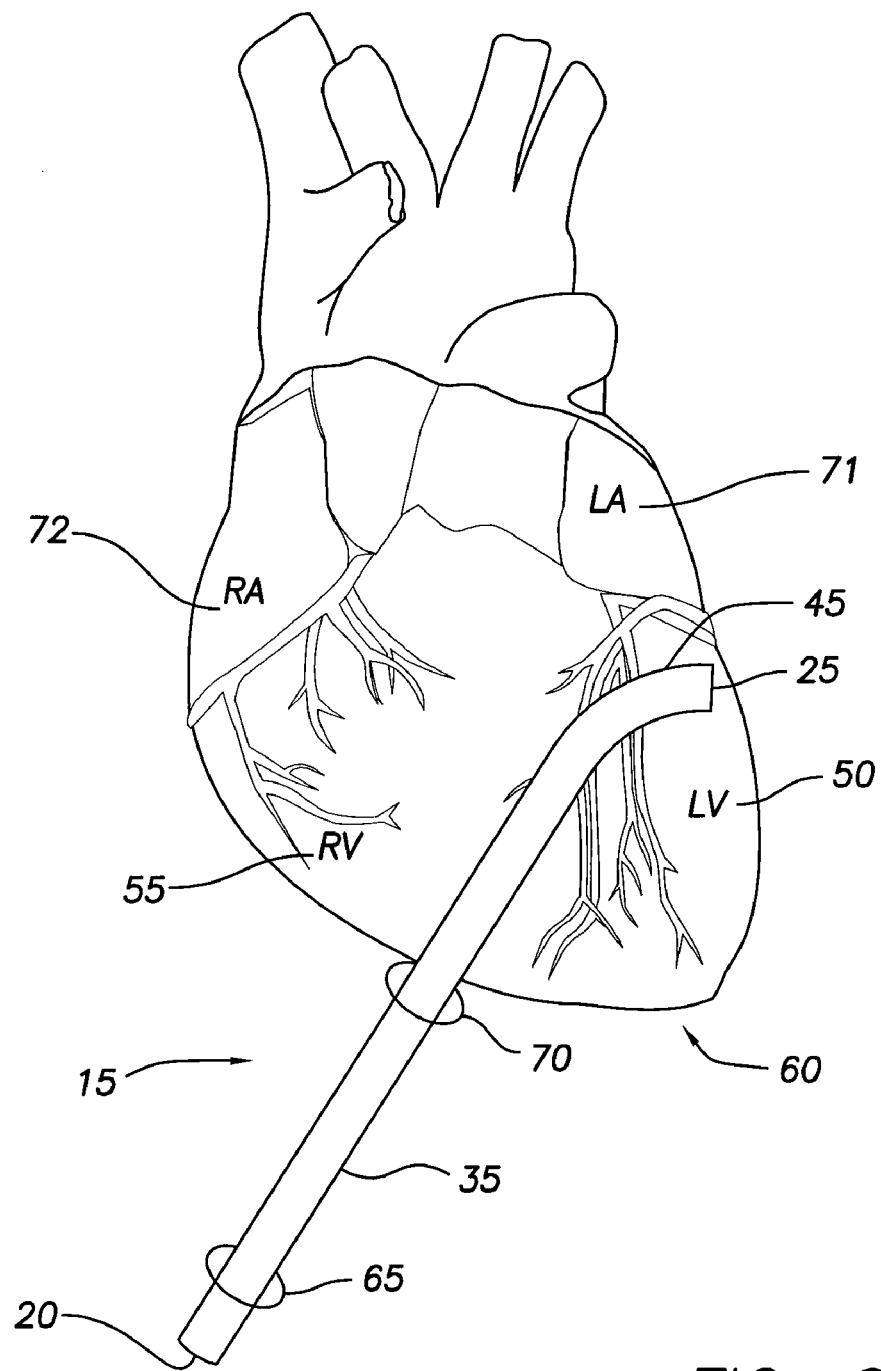
Figure 7A:
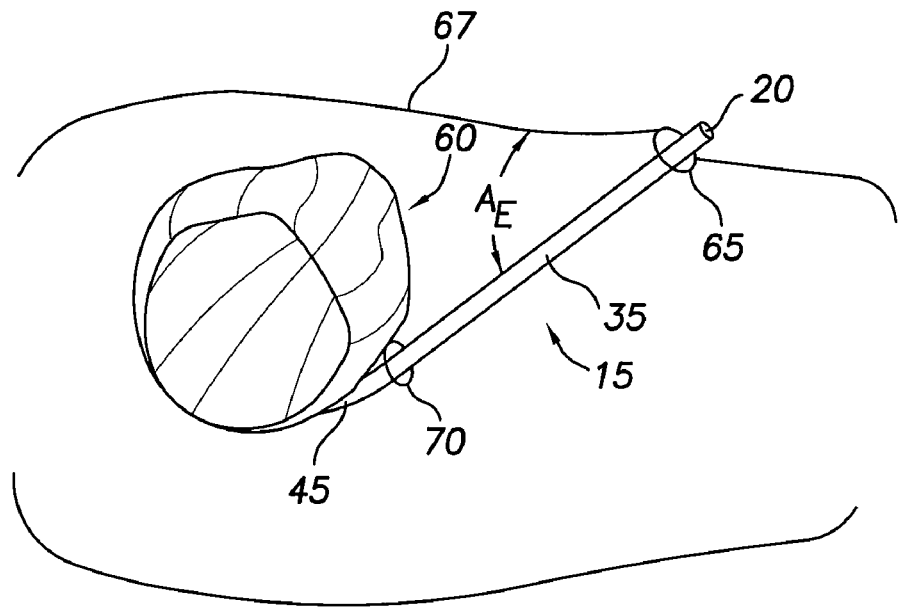
FIGS. 7A-7C illustrate various views of the second embodiment of the tubular body laying next to the left and right ventricle portions of a patient's heart as the tubular body makes a posterior approach to the heart from a subxiphoid opening in the patient's chest wall.
Figure 7B:
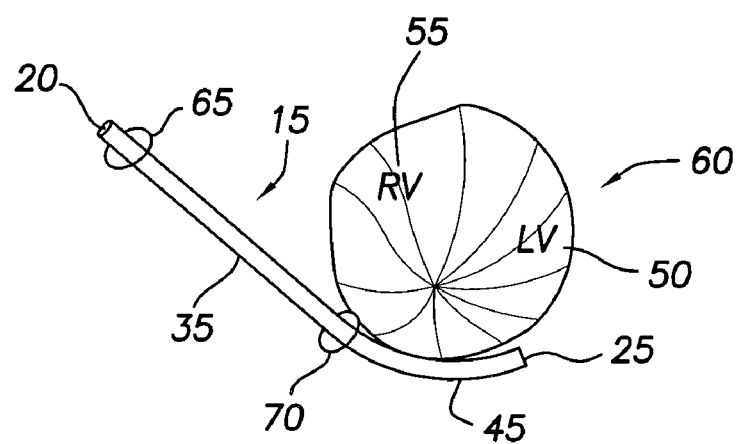
Figure 7C:
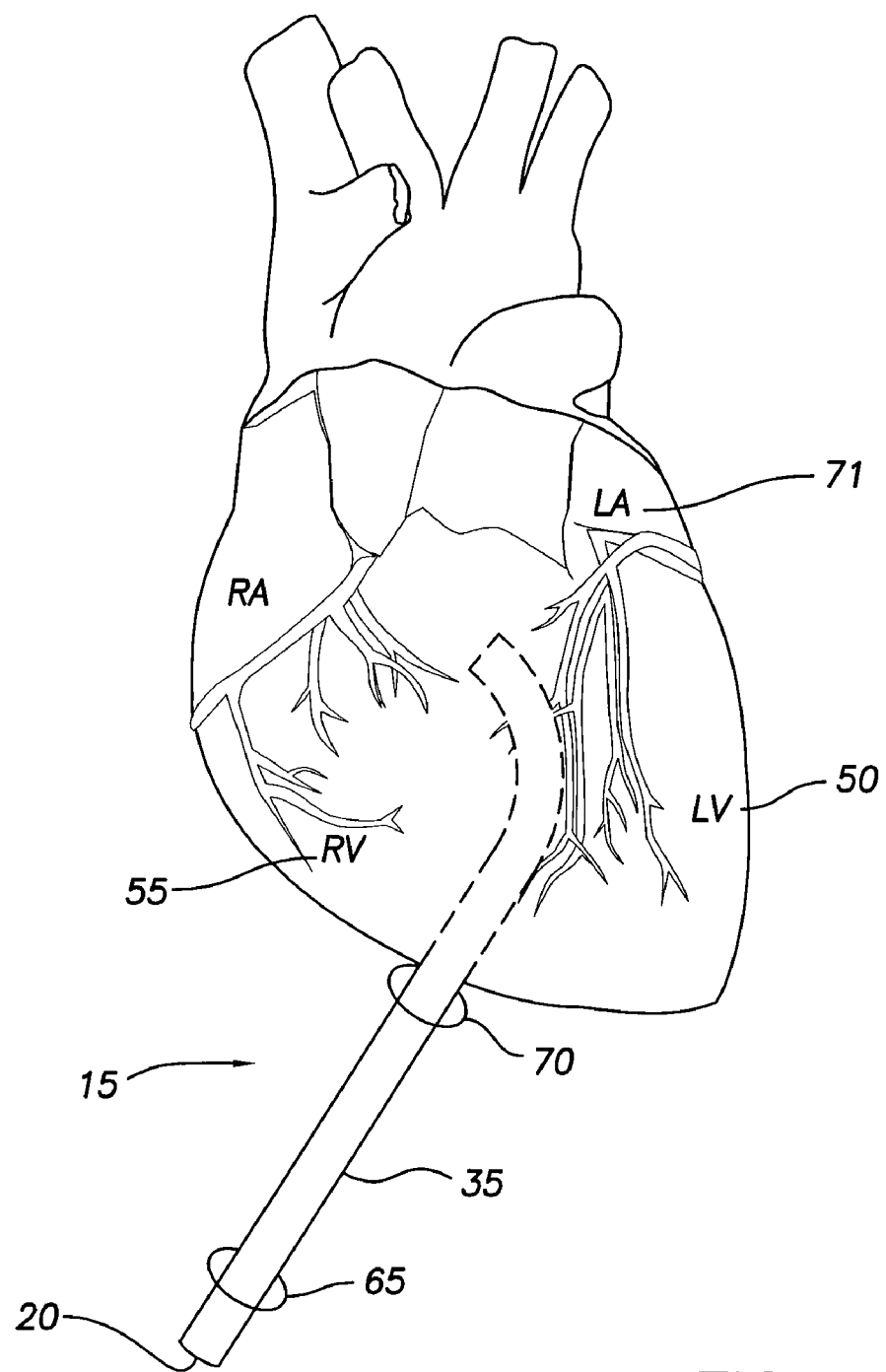

6A-6C and 7A-7C. FIGS. 6A-6C illustrate various views of the second embodiment of the tubular body 15 laying next to the left and right ventricle portions 50, 55 of a patient's heart 60 as the tubular body 15 makes an anterior approach to the heart 60 from a subxiphoid opening 65 in the patient's chest wall 67. FIGS. 7A-7C illustrate various views of the second embodiment of the tubular body 15 laying next to the left and right ventricle portions 50, 55 of a patient's heart 60 as the tubular body 15 makes a posterior approach to the heart 60 from a subxiphoid opening 65 in the patient's chest wall 67.

As can be understood in FIGS. 6A-6C and 7A-7C, in one embodiment, the tubular body 15 enters the subxiphoid opening 65 at a subxiphoid entry angle $A_E$ of between approximately 40 degrees and approximately 50 degrees. The curved portion 45 of the tubular body 15 lies next to, and generally matches, the heart ventricle surfaces 50, 55. The proximal zone 35 resides in the subxiphoid subcutaneous area, the transition point between the proximal and distal zones 35, 45 sits at the pericardial sac opening 70, and the distal zone 45 resides in the pericardial space.

Because of the curved configuration of the tubular body 15 and the differences in rigidity between the zones 35, 45 of the tubular body 15, the second embodiment of the tubular body 15 is able to sweep within the pericardial sac up to approximately 360 degrees around the heart 60 with respect to the pericardial sac entry point and/or the subxiphoid access point. Also, the curved portion 45 can be swept about the heart anterior to posterior, or vice versa. As a result, the second embodiment of the tubular body 15 can be used to deliver a medical device or therapy (e.g., pacing or defibrillation leads, myocardial infarction patches, ablation catheters, mapping catheters, fiber optic video cameras, drugs, etc.) to any location, or nearly any location, on the epicardial surface of the heart, including the right and left ventricle surfaces and the right and left atrium surfaces. Also, the second embodiment of the tubular body 15 can be used to gently loosen pericardial adhesions at any location, or nearly any location, in the pericardial space and prepare the pericardial space for delivery of the medical device and/or therapy. In one embodiment, the curved portion 45 of the tubular body 15 is configured to lie next to, and generally match, the heart ventricle surfaces 50, 55 and/or the heart atrium surfaces 71, 72. In one embodiment, where the curved portion 45 is configured to lie next to, and generally match, both the ventricle and atrium surfaces 50, 55, 71, 72, the curved portion 45 is sufficiently supple to conformingly adapt between the ventricle surfaces 50, 55 and the atrium surfaces 71, 72.

The single curve design depicted in FIG. 5 can be used to allow some flexibility in medical device placement and maneuverability provided by the sheath 10. If the single curve tubular body 15 is slightly rotated clockwise or counterclockwise, the tubular body distal end 25 and medical device trajectories shift from side to side.

To insert the tubular body 15 of the sheath 10 into the pericardial space of the patient, a Touhy needle is used to create entry holes in the high abdominal region near the patient's xiphoid process and in the pericardial sac of the patient. A guidewire is routed through the Touhy needle into the pericardial space and the needle is withdrawn, leaving behind the guidewire to define a pathway to the pericardial space. The straightened out sheath 10 tracks down a guidewire into the pericardial space.

Regardless of whether the first tubular body embodiment (e.g., FIGS. 1 and 2) or the second tubular body embodiment (e.g., FIG. 5) is being employed, the tubular body 15 of the sheath 10 can be straightened to a greater or lesser extent via a straight dilator when the sheath 10 is being inserted into the pericardial space. In one embodiment, the straight dilator is flexible and while the dilator straightens the sheath to some extent, slight curvature still remains in the sheath (i.e., in one embodiment, the flexible dilator is not able completely or fully straighten the sheath).

Once the Touhy needle is withdrawn from the patient, the sheath 10 tracks down a guidewire into the pericardial space. Once inside the pericardial space, the dilator is removed from the sheath 10 and the tubular body 15 is allowed to fully return its curved shape.

Regardless of whether the first tubular body embodiment (e.g., FIGS. 1 and 2) or the second tubular embodiment (e.g., FIG. 5) is being employed, the physician can then rotate and/or push/pull the sheath 10 to direct the distal end of the tubular body 15 to different locations within the pericardial space. Specifically, the physician can rotate and slightly manipulate the proximal end of the sheath extending from the patient to cause the distal end of the sheath to sweep about the heart. In one embodiment, to rotate and otherwise manipulate the proximal end of the sheath, the physician will grasp the hemostasis valve.

Figure 8:
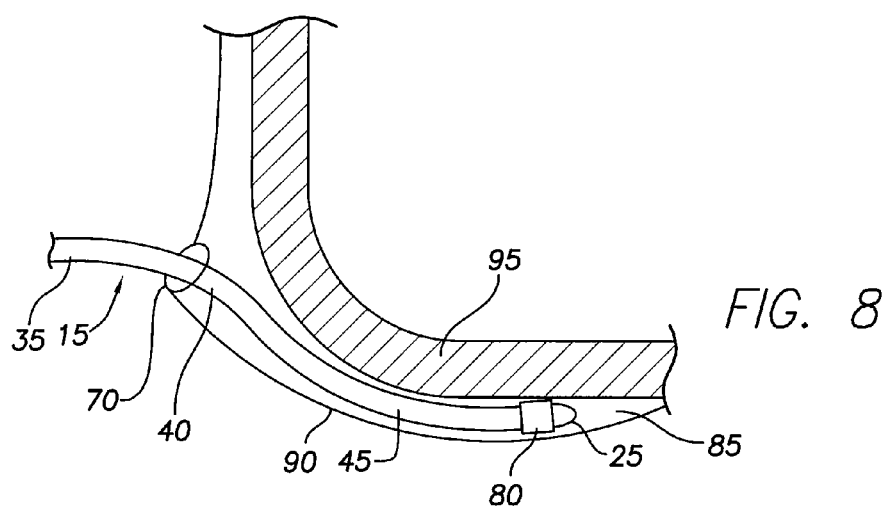
FIG. 8 is a cross-sectional elevation taken through the pericardial space when a distal zone of the tubular body has entered the pericardial space.
Figure 9:
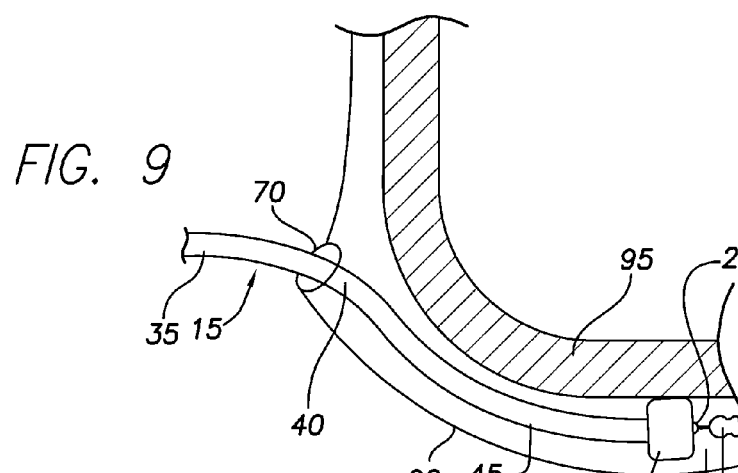
FIG. 9 is the same view depicted in FIG. 8, except the pericardial space has been expanded via an inflatable balloon.

For a discussion of a pericardial space expansion feature 80 that may exist on any one or more of the embodiments of the tubular bodies 15 disclosed in this Detailed Description, reference is made to FIGS. 8 and 9. FIG. 8 is a cross-sectional elevation taken through the pericardial space 85 when a distal zone 45 of the tubular body 15 has entered the pericardial space 85. FIG. 9 is the same view depicted in FIG. 8, except the pericardial space 85 has been expanded via an inflatable balloon 80.

As shown in FIG. 8, in one embodiment, a donut-like inflatable balloon 80 is provided near the distal end 25 of the tubular body 15, and the distal zone 45 of the tubular body 15 enters the opening 70 in the pericardial sac 90 in a deflated or unexpanded condition. As indicated in FIG. 9, once the distal zone 45 is securely in the pericardial space 85, the balloon 80 is expanded to separate the pericardial sac 90 from the heart wall 95, thereby increasing the clearance in the pericardial space 85 for the delivery of a medical device (e.g., lead) 100 or therapy.

Figure 9A:
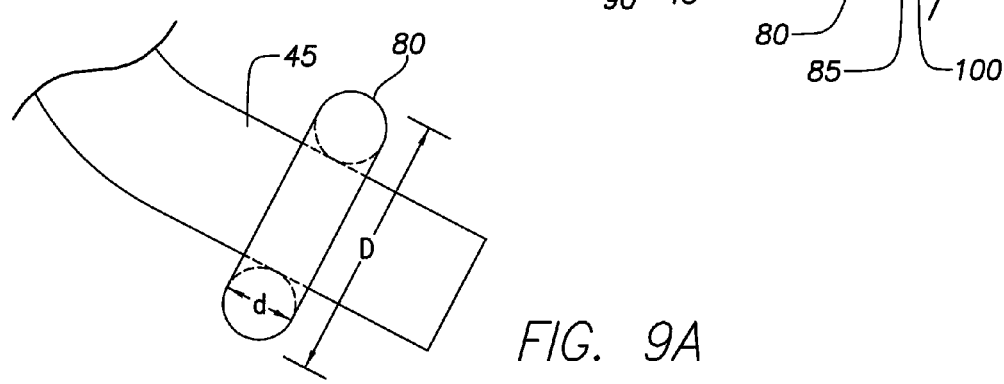
FIG. 9A is an enlarged cross-section view of the balloon depicted in FIG. 9.

For a more detailed discussion regarding the configuration of one embodiment of the balloon 80, reference is made to FIG. 9A, which is an enlarged cross-section view of the balloon 80 depicted in FIG. 9. As can be understood from FIG. 9A, when the balloon is inflated, the balloon 80 has a first diameter D of between approximately 0.125 inch and approximately 0.5 inch and a second diameter d of between approximately 0.01 inch and approximately 0.03 inch. When the balloon is un-inflated, the balloon has a first diameter D of between approximately 0.065 inch and approximately 0.09 inch and a second diameter d of between approximately 0.006 inch and approximately 0.02 inch. In one embodiment, the balloon 80 has a material or sheet thickness of between approximately 0.001 inch and approximately 0.01 inch. In one embodiment, the balloon 80 is made of a polymer material such as silicone rubber, isoprene, chronoprene, polyurethane, or etc. In one embodiment, the balloon 80 is placed in fluid communication with a pressurization pump exterior to the patient and sheath 10 via a lumen that extends through the length of the wall of the tubular body 15. The pressurization pump inflates and deflates the balloon 80. Inflating/deflating the balloon can also be accomplished by using a syringe, which is readily available.

Figure 10:
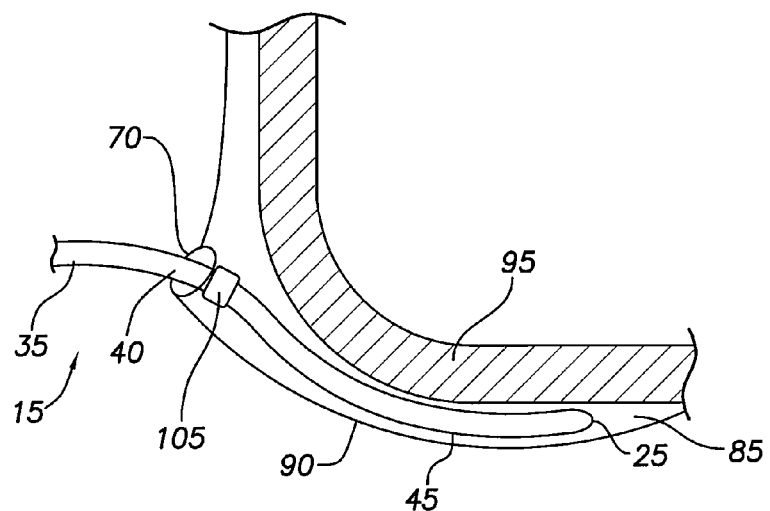
FIG. 10 is a cross-sectional elevation taken through the pericardial space when a distal zone of the tubular body has entered the pericardial space.
Figure 11:
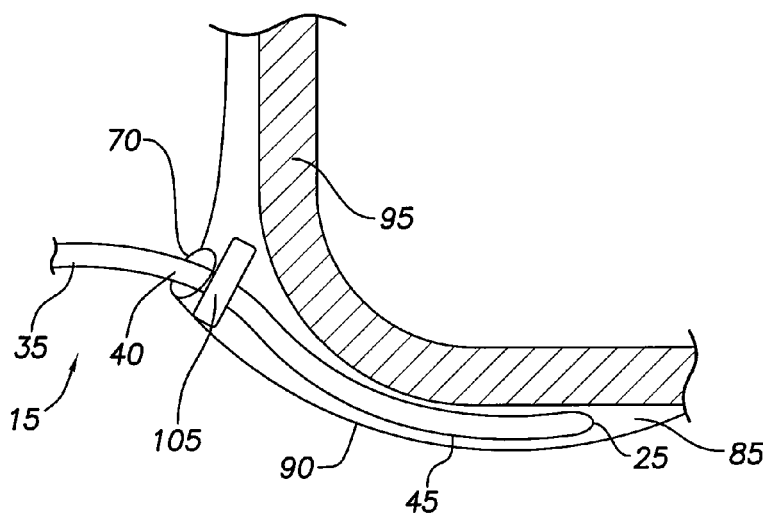
FIG. 11 is the same view depicted in FIG. 10, except the tubular body is prevented from being withdrawn from the pericardial space via an expanded inflatable balloon.

For a discussion of an expansion feature 105 for preventing unintentional withdrawal of the tubular body 15 from the pericardial space 85, reference is made to FIGS. 10 and 11. FIG. 10 is a cross-sectional elevation taken through the pericardial space 85 when a distal zone 45 of the tubular body 15 has entered the pericardial space 85. FIG. 11 is the same view depicted in FIG. 10, except the tubular body 15 is prevented from being withdrawn from the pericardial space 85 via an expanded inflatable balloon 105.

As depicted in FIG. 10, a donut-like inflatable balloon 105 is located in the intermediate zone 40 (in the context of the tubular body embodiment depicted in FIGS. 1-2) or at the transition point between the proximal and distal zones 35, 45 (in the context of the tubular body embodiment depicted in FIG. 5). As shown in FIG. 10, the balloon 105 passes through the pericardial sac opening 70 in a deflated condition. The tubular body 15 is positioned such that the deflated balloon 105 resides within the pericardial space 85 adjacent the opening 70 in the pericardial sac 90. Once the tubular body 15 is so positioned, the balloon 105 is inflated to its expanded condition as shown in FIG. 11, thereby preventing the withdrawal of the distal zone 45 of the tubular body 15 from the pericardial space 85.

Figure 12:
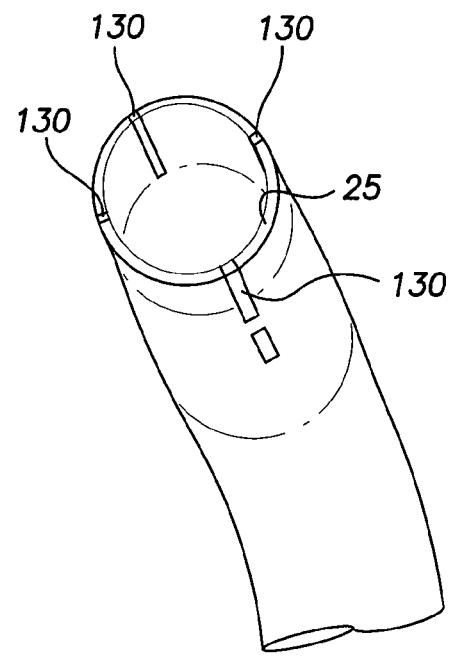
FIG. 12 is an end isometric view of the one embodiment of an atraumatic tip.
Figure 13:
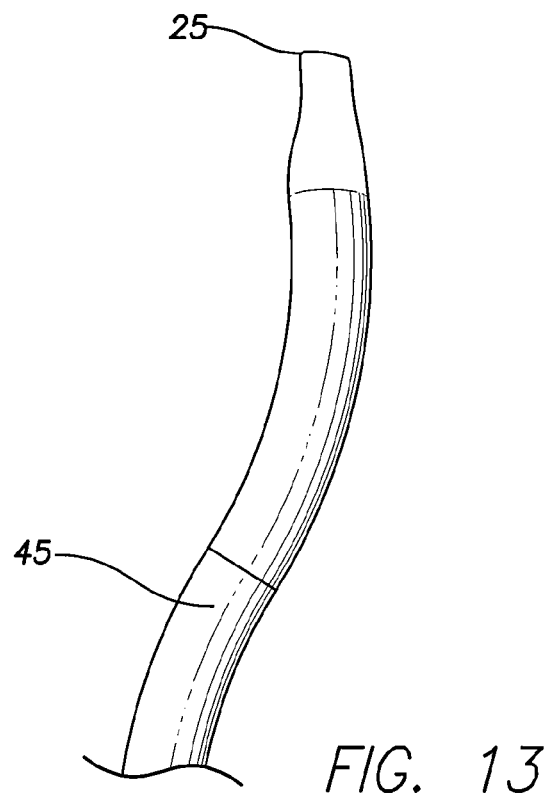
FIG. 13 is a side view of another embodiment of an atraumatic tip.

For a discussion of an atraumatic tip 25 that serves as the distal end 25 of any of the previously described tubular bodies 15, reference is made to FIGS. 12 and 13. FIG. 12 is an end isometric view of the one embodiment of an atraumatic tip 25. FIG. 13 is a side view of another embodiment of an atraumatic tip 25.

As shown in FIGS. 12 and 13, in one embodiment, the atraumatic tip 25 is made from a polymer material that is softer than the polymer material of the distal zone 45. In one embodiment, the atraumatic tip 25 is formed from a polymer material such as silicone rubber, PEBAX, polyethylene, nylon, or etc. In one embodiment, the atraumatic tip 25 has a durometer of approximately 25 Shore D.

As can be understood from FIG. 13, in one embodiment, the atraumatic tip 25 extends approximately 0.5 centimeter past the distal end of the distal zone 45. As can be understood from FIG. 12, in one embodiment, the atraumatic tip 25 includes radiopaque strips 130 that are a polymer material loaded with a radiopaque material (e.g., tungsten, platinum, or etc.) to make the tip visible via fluoroscopy. The atraumatic tip 25 is slightly tapered and has rounded edges to prevent damage to the heart.

Figure 14:
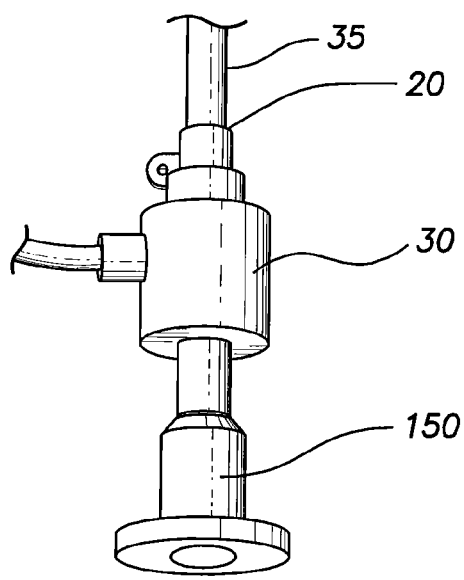
FIG. 14 is a side isometric view of the valve by-pass tool employed with the hemostasis valve.
Figure 15:
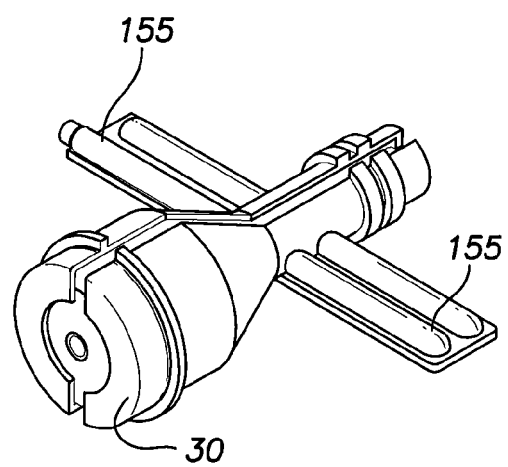
FIG. 15 is an end isometric view of the splittable hemostasis valve.
Figure 16:
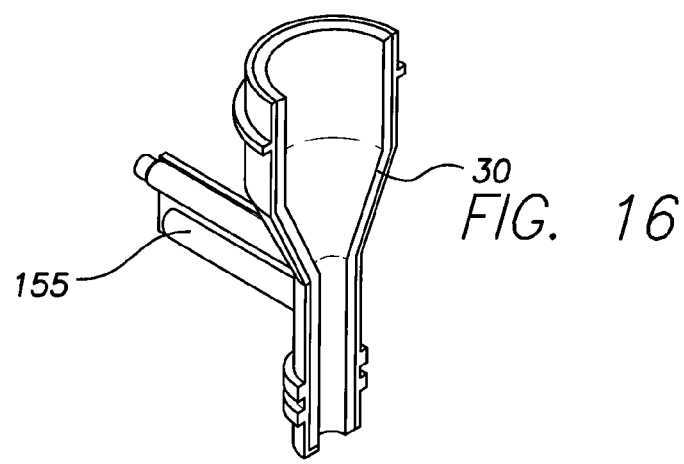
FIG. 16 is a side isometric view of half of the splittable hemostasis valve after being split.

For a discussion of a valve by-pass tool 150 and a hemostasis valve 30 for use with any of the previously described tubular bodies 15, reference is made to FIGS. 14-16. FIG. 14 is a side isometric view of the valve by-pass tool 150 employed with the hemostasis valve 30. FIG. 15 is an end isometric view of the splittable hemostasis valve 30. FIG. 16 is a side isometric view of half of the splittable hemostasis valve 30 after being split.

As shown in FIG. 14, the valve by-pass tool 150 is received in the proximal opening of the hemostasis valve 30 and opens up the silicone seal in the valve 30. A medical device (e.g., a lead) can then be inserted through the passage extending through the tool 150 to easily pass through the valve 30 and into the lumen of the tubular body 15. After the distal end of the lead has entered the tubular body 15, the tool 150 can be pulled out of the valve 30 to close the silicone seal about the lead and reduce the amount of fluid (e.g., air) going into or out of the pericardial space. The valve by-pass tool 150 can be reintroduced into the valve 30 as the tubular body 15 is pulled out of the chest cavity and past the proximal connector end of the medical device (e.g., lead).

In one embodiment, the hemostasis valve 30 is removable from the proximal end 20 of the tubular body 15. In one embodiment, as depicted in FIGS. 15 and 16, the hemostasis valve 30 is splittable to facilitate the valve 30 being removed from about a medical device implanted in the patient. In one embodiment, the valve 30 has wings 155 to facilitate its splitting. For greater detail regarding the splittable embodiment of the hemostasis valve 30, see U.S. patent application Ser. No. 11/029,800, which was filed Jan. 4, 2005 and is incorporated into this Detailed Description in its entirety.

In one embodiment, the tubular body 15 has a slick inner surface defining its lumen. The low friction between the lumen of the tubular body 15 facilitates the easy, non-binding passage of a medical device through the tubular body 15.

In one embodiment, the distal end 25 of the tubular body 15 includes a fiber optic camera. The camera allows for the visualization of the lead placement location and to avoid coronary arteries, fat or other obstacles within the pericardial space.

In one embodiment, the tubular body 15 is peelable or splittable as disclosed in PCT Applications 2006/016373 and 2006/016372, both of which are hereby incorporated into this Detailed Description in their entireties, and claim the benefit of U.S. Provisional Patent Applications 60/675,973 and 60/677,423, respectively.

After a lead or other type of medical device is implanted in the pericardial space, the sheath 10 is gently pulled back until it exits the pericardial sac and the skin just below the coastal margin. The sheath 10 and hemostasis valve 30 can then be split to allow their removal from about the lead. Alternatively, the sheath 10 and hemostasis valve 30 can be removed in one piece by using the valve by-pass tool 150 to allow the lead suture sleeve and lead connector to pass through the valve 30.

Figure 17:
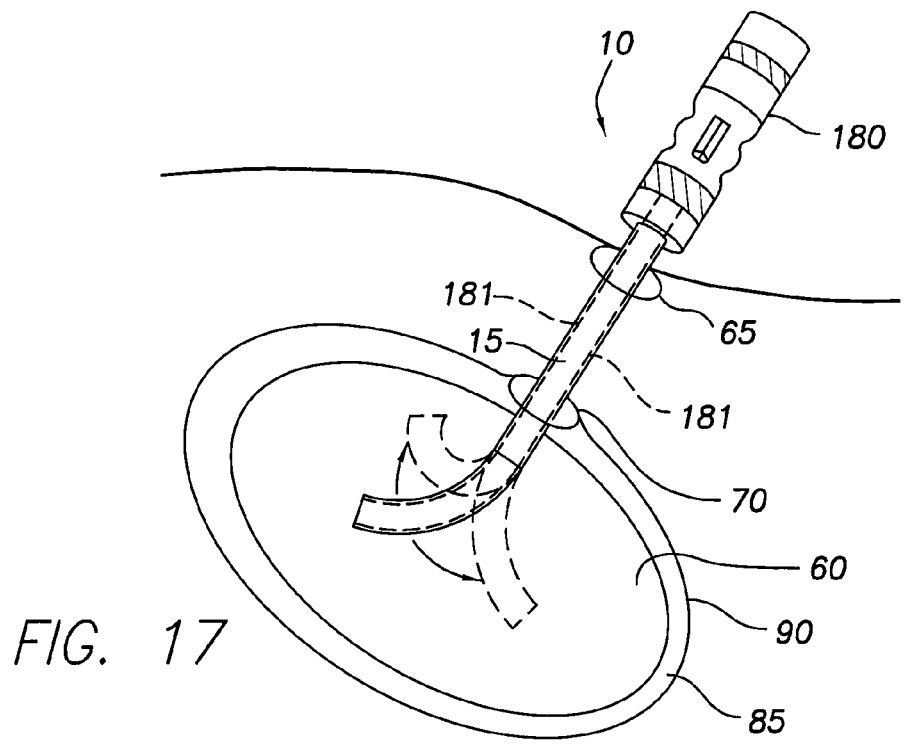
FIG. 17 is a diagrammatic depiction of the hand control equipped sheath being employed.

For a discussion of a sheath 10 having a deflection hand control 180, reference is made to FIG. 17, which is a diagrammatic depiction of the hand control equipped sheath being employed. In one embodiment, the hand control 180 simply provides a gripping surface for the physician to grasp the sheath 10 and torque, push and pull the sheath 10.

In one embodiment, the handle 180 is coupled to deflection wires 181 longitudinally extending through the walls of the tubular body 15. Manipulating the handle 180 displaces the wires 181 within the walls and deflects the distal end of the tubular body. In one embodiment, the handle 180 serves to manipulate an inner and/or outer tubular body as provided for in the following discussion regarding a sheath-in-sheath introducer.

Figure 18:
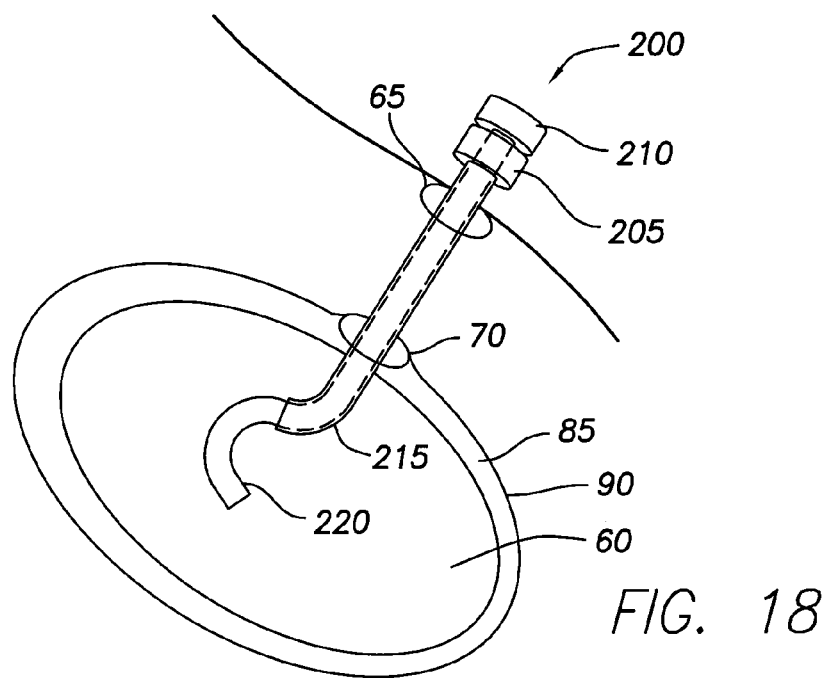
FIG. 18 is a diagrammatic depiction of a double sheath introducer being employed.

For a discussion of a sheath-in-sheath introducer 200, reference is made to FIG. 18, which is a diagrammatic depiction of the introducer 200 being employed. As shown in FIG. 18, in one embodiment, the introducer 200 includes two sheaths 205, 210, each sheath employing a curved tubular body 215, 220. The internal tubular body 220 is longer and softer than the outer tubular body 215.

A dilator is inserted in the tubular body 215 of the outer sheath 205, which is then inserted through the subxiphoid and pericardial sac openings 65, 70. Once the distal end of the tubular body 215 of the outer sheath 205 is in the pericardial space 85, the dilator is withdrawn from the outer tubular body 215. The tubular body 220 of the inner sheath 210 is then inserted into the tubular body 215 of the outer sheath 205 such that the inner tubular body 220 protrudes from the outer tubular body 215 inside the pericardial space 85.

As previously mentioned, both tubular bodies 215, 220 are curved and the inner tubular body 220 is longer and softer than the outer tubular body 215. Consequently, rotating the tubular bodies 215, 220 relative to each other and/or longitudinally extending or retracting the tubular bodies 215, 220 relative to each other changes the overall shape and orientation of the introducer 200.

In one embodiment, one or both of the sheaths 205, 210 will employ double or single curved tubular bodies as discussed with respect to FIGS. 1, 2 and 5. In one embodiment, the tubular bodies 205, 210 will have generally rigid proximal zones and softer curved distal zones, as discussed with respect to FIGS. 1, 2 and 5.

Although the present invention has been described with reference to preferred embodiments, persons skilled in the art will recognize that changes may be made in form and detail without departing from the spirit and scope of the invention.

What is claimed is:

1. An introducer sheath having a curved portion configured to generally match the curved epicardial surface of a heart, said sheath comprising a tubular body having a longitudinal axis extending there through, the tubular body including a proximal zone having a distal end, an intermediate zone having a distal end and a distal zone having a distal end defining an opening at the distal tip of the tubular body, wherein the proximal zone is generally straight along its entire length ($L_{PZ}$), the intermediate zone extends from the distal end of the proximal zone and curves along its entire length ($L_{IZ}$) in a first direction, and the distal zone extends from the distal end of the intermediate zone and curves along its entire length ($L_{DZ}$) in a second direction different from the first direction, wherein the combined effect of the curves of the intermediate and distal zones results in the portion of the longitudinal axis extending through the distal tip of the tubular body being nearly parallel to the portion of the longitudinal axis extending through the proximal zone, wherein the length of the intermediate zone ($L_{IZ}$) is less than the length of the distal zone ($L_{DZ}$) and the length of the distal zone ($L_{DZ}$) is less than the length of the proximal zone ($L_{PZ}$), and wherein the intermediate zone and the distal zone define the curved portion and the curved portion is arranged with respect to the proximal zone so as to sweep about the heart upon rotation of the proximal zone about the longitudinal axis.

2. The sheath of claim 1, wherein the length of the intermediate zone ($L_{IZ}$) is approximately 2.5 centimeters and the length of the distal zone ($L_{DZ}$) is approximately 4.8 centimeters.

3. The sheath of claim 1, wherein the portion of the longitudinal distal extending through the distal tip end of the tubular body is anywhere from greater than zero degrees to approximately twenty degrees from being parallel to the portion of the longitudinal axis extending through the proximal zone.

4. The sheath of claim 1, wherein the proximal zone is more rigid than the entire intermediate zone and the entire intermediate zone is more rigid than the distal zone.

5. The sheath of claim 1, further comprising an atraumatic tip extending from the distal end of the distal zone and wherein the tip is less rigid than the distal zone.

6. The sheath of claim 1, further comprising an inflatable balloon coupled to the tubular body nearer a transition between the proximal and intermediate zones than the distal zone.

7. The sheath of claim 1, wherein the second direction is reversed with respect to the first direction.

8. The sheath of claim 1, wherein the length of the intermediate zone ($L_{IZ}$) is between approximately two centimeters and approximately six centimeters.

9. The sheath of claim 1, wherein the length of the distal zone ($L_{DZ}$) is between approximately two centimeters and approximately ten centimeters.

10. The sheath of claim 1 wherein the length of the proximal zone ($L_{PZ}$) is between approximately eight centimeters and 18 centimeters.

11. The sheath of claim 1 wherein the length of the proximal zone ($L_{PZ}$) is approximately ten centimeters.

12. The sheath of claim 1 wherein the portion of the longitudinal axis extending through the distal tip end of the tubular body is approximately ten degrees from being parallel to the portion of the longitudinal axis extending through the proximal zone.

13. The sheath of claim 1 wherein the distal end of the distal zone is offset from the distal end of the proximal zone a linear distance D of approximately 6.4 centimeters.

14. The sheath of claim 1 wherein the distal end of the distal zone is offset from the distal end of the proximal zone a linear distance D of between approximately five centimeters and approximately 14 centimeters.

15. An introducer sheath having a curved portion configured to generally match the curved epicardial surface of a heart, said sheath comprising a tubular body having a longitudinal axis extending there through, the tubular body including a proximal zone having a distal end, an intermediate zone having a distal end and a distal zone having a distal end defining an opening at the distal tip of the tubular body, wherein the proximal zone is generally straight along its entire length ($L_{PZ}$), the intermediate zone extends from the distal end of the proximal zone and curves along its entire length over a radius ($R_{IZ}$), in a first direction to define an angle of curvature ($A_{IZ}$), and the distal zone extends from the distal end of the intermediate zone and curves along its entire length over a radius ($R_{DZ}$) in a second direction different from the first direction to define an angle of curvature ($A_{DZ}$), wherein the combined effect of the curves of the intermediate and distal zones results in the portion of the longitudinal axis extending through the distal tip of the tubular body being nearly parallel to the portion of the longitudinal axis extending through the proximal zone, wherein the angle of curvature of the intermediate zone ($A_{IZ}$) is less than the angle of curvature of the distal zone ($A_{DZ}$) and the length of the distal zone is less than the length of the proximal zone, and wherein the intermediate zone and the distal zone define the curved portion and the curved portion is arranged with respect to the proximal zone so as to sweep about the heart upon rotation of the proximal zone about the longitudinal axis.

16. The sheath of claim 15, wherein the angle of curvature of the intermediate zone ($A_{IZ}$) is approximately 45 degrees and the angle of curvature of the distal zone ($A_{DZ}$) is approximately 55 degrees.

17. The sheath of claim 15, wherein the angle of curvature of the intermediate zone ($A_{IZ}$) is between approximately 30 degrees and approximately 60 degrees.

18. The sheath of claim 15, wherein the angle of curvature of the distal zone ($A_{DZ}$) is between approximately 30 degrees and approximately 85 degrees.

19. The sheath of claim 15 wherein the portion of the longitudinal axis extending through the distal tip end of the tubular body is approximately ten degrees from being parallel to the portion of the longitudinal axis extending through the proximal zone.

20. The sheath of claim 15 wherein the intermediate zone curves over a radius ($R_{IZ}$) of between approximately two centimeters and approximately five centimeters.

21. The sheath of claim 15 wherein the intermediate zone curves over a radius ($R_{IZ}$) of approximately 2.8 centimeters.

22. The sheath of claim 15 wherein the distal zone curves over a radius ($R_{DZ}$) of between approximately two centimeters and approximately eight centimeters.

23. The sheath of claim 15 wherein the distal zone curves over a radius ($R_{DZ}$) of approximately 4.6 centimeters.

24. The sheath of claim 15 wherein:
the distal zone curves over a radius ($R_{DZ}$) of between approximately two centimeters and approximately eight centimeters;
the intermediate zone curves over a radius ($R_{IZ}$) of between approximately two centimeters and approximately five centimeters
the angle of curvature of the distal zone ($A_{DZ}$) is between approximately 30 degrees and approximately 85 degrees;
the angle of curvature of the intermediate zone ($A_{IZ}$) is between approximately 30 degrees and approximately 60 degrees;
the length of the proximal zone ($L_{PZ}$) is between approximately eight centimeters and 18 centimeters.

* * * * *